United States Patent
Liang et al.

(10) Patent No.: US 12,228,572 B2
(45) Date of Patent: Feb. 18, 2025

(54) ENHANCED EXPRESSION OF POLO-LIKE KINASE 3 (PLK3) IN HUMAN IMMUNODEFICIENCY VIRUS (HIV)-INFECTED CELLS

(71) Applicant: THE FIRST HOSPITAL OF CHINA MEDICAL UNIVERSITY, Shenyang (CN)

(72) Inventors: Guoxin Liang, Shenyang (CN); Hong Shang, Shenyang (CN)

(73) Assignee: THE FIRST HOSPITAL OF CHINA MEDICAL UNIVERSITY, Shenyang (CN)

(*) Notice: Subject to any disclaimer, the term of this patent is extended or adjusted under 35 U.S.C. 154(b) by 0 days.

(21) Appl. No.: 18/292,949

(22) PCT Filed: Sep. 30, 2021

(86) PCT No.: PCT/CN2021/122082
§ 371 (c)(1),
(2) Date: Jan. 29, 2024

(87) PCT Pub. No.: WO2023/004994
PCT Pub. Date: Feb. 2, 2023

(65) Prior Publication Data
US 2024/0264171 A1    Aug. 8, 2024

(30) Foreign Application Priority Data
Jul. 28, 2021 (CN) .......................... 202110855712.1

(51) Int. Cl.
G01N 33/569 (2006.01)
A61P 31/18 (2006.01)
G01N 33/68 (2006.01)

(52) U.S. Cl.
CPC ........ *G01N 33/56988* (2013.01); *A61P 31/18* (2018.01); *C12Y 207/11021* (2013.01); *G01N 33/6893* (2013.01); *C12N 2740/16011* (2013.01); *G01N 2333/16* (2013.01); *G01N 2333/912* (2013.01)

(58) Field of Classification Search
CPC .............. C12Y 207/11021; C12N 2740/16011
See application file for complete search history.

(56) References Cited

U.S. PATENT DOCUMENTS

| | | |
|---|---|---|
| 2011/0053944 A1 | 3/2011 | Caruso et al. |
| 2011/0229484 A1 | 9/2011 | Baumert et al. |
| 2014/0011812 A1 | 1/2014 | Regev et al. |

FOREIGN PATENT DOCUMENTS

| | | |
|---|---|---|
| CN | 101208317 A | 6/2008 |
| CN | 102227237 A | 10/2011 |
| CN | 104069106 A | 10/2014 |
| CN | 109374896 A | 2/2019 |
| CN | 110343175 A | 10/2019 |
| CN | 111500706 A | 8/2020 |
| EP | 3636781 A1 | 4/2020 |
| WO | 2016135046 A1 | 9/2016 |

OTHER PUBLICATIONS

Hu J, Wang G, Liu X, Zhou L, Jiang M, Yang L. Polo-like kinase 1 (PLK1) is involved in toll-like receptor (TLR)-mediated TNF-α production in monocytic THP-1 cells. PLoS One. Oct. 18, 2013;8(10):e78832. (Year: 2013).*
UniProtKB/Swiss-Prot: Q9H4B4.2 2024 (Year: 2024).*
NP_004064.2, serine/threonine-protein kinase PLK3 [*Homo sapiens*], GenPept, 2022.
Dawei Zhou, et al., Inhibition of Polo-like kinase 1 (PLK1) facilitates the elimination of HIV-1 viral reservoirs in CD4+ T cells ex vivo, Sicence Advances, 2020, pp. 1-16, vol. 6, No. 29.
Pavel Bostik, et al., Dysregulation of the Polo-Like Kinase Pathway in CD4+ T Cells Is Characteristic of Pathogenic Simian Immunodeficiency Virus Infection, Journal of Virology, 2004, pp. 1464-1472, vol. 78, No. 3.
Jin Gohda, et al., BI-2536 and BI-6727, dual Polo-like kinase/bromodomain inhibitors, effectively reactivate latent HIV-1, Scientific Reports, 2018, pp. 1-13, 8:3521.

* cited by examiner

*Primary Examiner* — Jeffrey S Parkin
(74) *Attorney, Agent, or Firm* — Bayramoglu Law Offices LLC

(57) ABSTRACT

Biomarker of HIV or SIV infected cells and its application are provided. The marker is PLK (polo-like kinase). By inhibiting the activity of a PLK protein or clearing the same, the purpose of releasing viruses without activating a repository is achieved, such that the viruses can be detected in a physiological state and can also be recognized and cleared by an immune system or a drug in vivo. Enhancing the activity of the PLK protein directly inhibits the release of viruses in an HIV and/or SIV-infected cell. The present invention provides a new target for diagnosis and antiviral therapy of HIV and/or SIV infection, provides medication basis and guarantee for the early rapid detection and extremely early treatment of virus infection, and has important clinical value.

2 Claims, 10 Drawing Sheets
Specification includes a Sequence Listing.

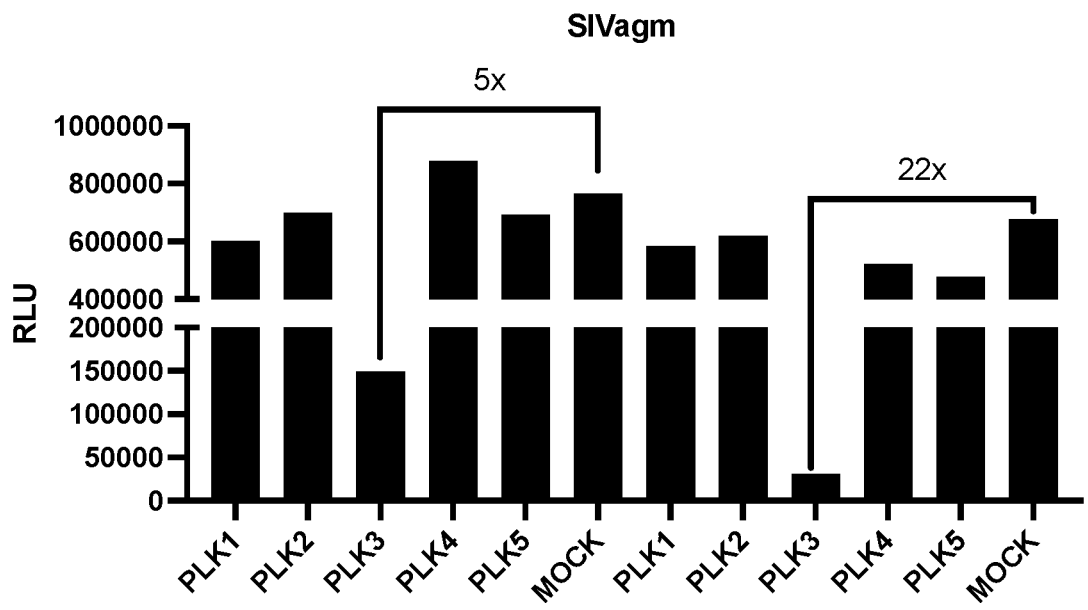
FIG. 15
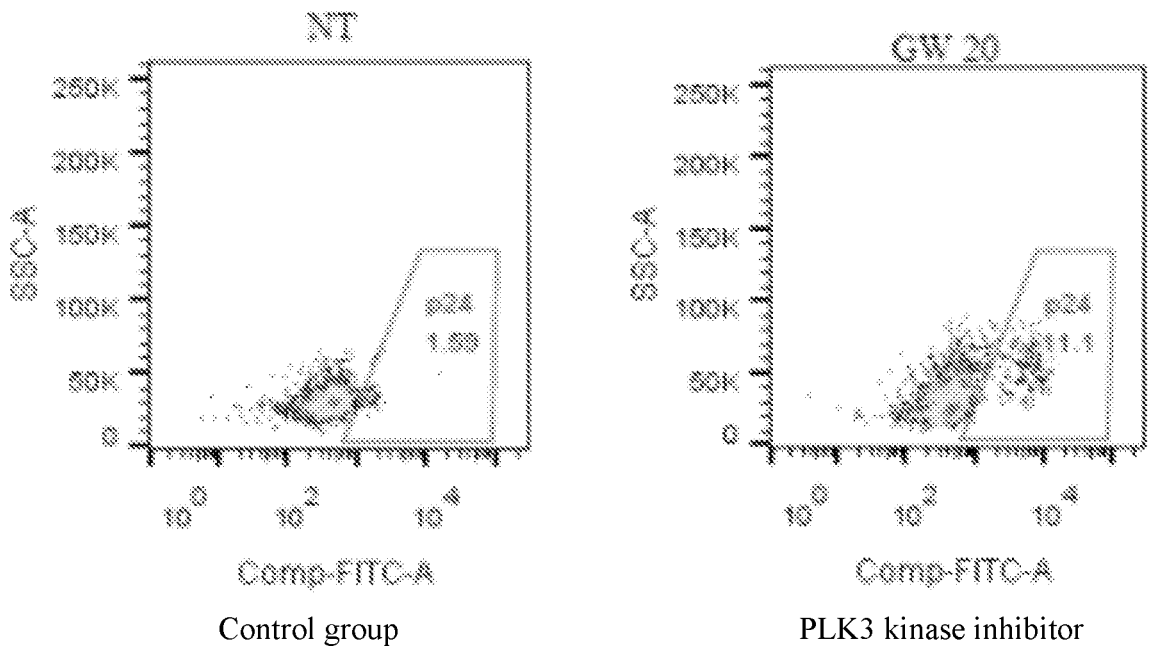
Control group
PLK3 kinase inhibitor
FIG. 16A
FIG. 16B

ENHANCED EXPRESSION OF POLO-LIKE KINASE 3 (PLK3) IN HUMAN IMMUNODEFICIENCY VIRUS (HIV)-INFECTED CELLS

CROSS REFERENCE TO THE RELATED APPLICATIONS

This application is the national phase entry of International Application No. PCT/CN2021/122082, filed on Sep. 30, 2021, which is based upon and claims priority to Chinese Patent Application No. 202110855712.1, filed on Jul. 28, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSYYT006_Sequence_Listing.txt, created on 01/26/2024, and is 5,899 bytes in size.

TECHNICAL FIELD

The present invention relates to the field of biomedicine. Specifically, the present invention relates to a marker in an HIV and/or SIV-infected cell and application of the marker. More specifically, the present invention provides use of a PLK protein in detecting an HIV and/or SIV-infected cell and clearing the cell, a method for treating an HIV and/or SIV-infected cell to detect and clear the cell, and a method for inhibiting the release of viruses in an HIV and/or SIV-infected cell.

BACKGROUND

HIV infection has become a major threat to global life and health. Current anti-HIV therapies can be used for only effectively controlling active replication of viruses, but cannot treat the infection completely. After HIV-infected patients receive highly active antiretroviral therapy (HAART), the load of viruses in plasma is decreased rapidly to be less than a minimum detection limit (<20 copies/mL). However, once antiviral therapy is stopped, viruses in the body will rapidly rebound. Therefore, most of AIDS patients require antiviral therapy in a whole life (except for a few elite controllers). The main reason why the viruses will rapidly rebound and the disease relapses and is difficult to cure after a drug is stopped is that "HIV repository cells" are present, which is also the most fundamental reason why AIDS is difficult to cure completely. Therefore, it is required to find effective and safe methods for detecting and clearing the HIV-infected repository cells.

According to existing methods for detecting an HIV repository, HIV repository cells are activated basically under laboratory conditions. For example, the HIV repository cells are activated by adding substances, such as phytohemagglutinin (PHA), to release a large number of progeny viruses, the number of the released viruses is detected, and then the approximate stock of the HIV repository cells is estimated. The detection method has the disadvantages that (1) standardization and quantification cannot be achieved; and (2) once the HIV repository cells are activated, although the release of the viruses can be promoted, important physiological characteristics of the HIV repository are lost. Therefore, the released viruses no longer have characteristics of latent viruses.

Researches have been conducted on methods using an internationally and widely recognized Shock&Kill therapy as a basic therapeutic principle in the field. Similar to existing detection methods, according to the Shock&Kill therapeutic principle, latent viruses in repository cells also need to be activated/shocked first by latent reversal agents (LRAs), and then discovered and cleared by CD8+T killer cells. However, during research of therapies, the key problem at present is that the LRAs used for activating latent viruses in CD4+T repository cells cannot specifically act on the repository cells, such that imbalance of body homeostasis or non-specific activation of a human immune system is caused. Thus, when the Shock&Kill therapy is adopted by using current strategies, imbalance of body homeostasis and immune disorders of patients, and even death, will be caused. Therefore, the Shock&Kill therapy has made success in basic experiments, but cannot be used in clinical treatment. A simian immunodeficiency virus (SIV), also known as an African green monkey virus, is an African primate retrovirus with similar properties to HIV.

In summary, finding a marker in an HIV and/or SIV-infected cell has important clinical significance in achieving the purposes that the release of a large number of progeny viruses can still be promoted without activating HIV repository cells or causing imbalance of body homeostasis, such that the cells can be detected under safe physiological conditions and can be recognized and cleared in vivo by an autoimmune system or a related antiviral drug, and the release of viruses in an HIV and/or SIV-infected cell is directly inhibited.

Polo-like kinase (PLK) is an important regulatory factor in cell cycle progression, and members in the family mainly include PLK1, PLK2, PLK3, PLK4 and PLK5. Some studies show that the PLK3 is related to cellular stress response and gene double-strand break repair. In cell lines, a PLK3 protein binds to a centrosome in a microtubule dependent manner, participates in mitosis and is positioned in a mitotic apparatus. Expression of kinase defective mutants leads to changes of microtubule dynamics and abnormal cell morphology induced by apoptosis. However, up to now, there are no reports about specific functional mechanisms of the PLK3 protein in HIV and/or SIV-infected cells and other information.

SUMMARY

In order to solve the above problems, the present invention provides a marker in an HIV and/or SIV-infected cell and application of the marker. The marker (namely, a PLK protein) is used in a method of treating an HIV and/or SIV-infected cell to enable the release of progeny viruses in the cell so as to detect and clear the cell, and a method capable of directly inhibiting the release of progeny viruses in an HIV and/or SIV-infected cell is provided.

In order to achieve the above purposes, the present invention provides the following technical schemes.

The present invention provides a marker in an HIV and/or SIV-infected cell, where the marker is a PLK protein.

Further, the marker PLK protein is a PLK3 protein.

Furthermore, the marker PLK3 protein is a PLK3-201 protein, and the PLK3-201 protein has an amino acid sequence shown in SEQ ID NO: 1.

The present invention further provides use of a substance capable of inhibiting the activity of a PLK protein in detecting and clearing an HIV and/or SIV-infected cell, where the substance capable of inhibiting the activity of a PLK protein includes at least one of the following substances in I-IV:

I, small molecule compounds,
II, PLK protein inhibitors, including: Wortmannin, Volasertib, BI2536, GW843682X, TAK960, Poloxin, LFM-A13, SEB13 Hydrochloride, TC-S 7005, TAK-960 dihydrochloride, SEB13 and TAK-960 hydrochloride;
III, specific antibodies or antigen-binding fragments against the PLK protein;
IV, siRNA or shRNA as a targeting inhibitor of the PLK protein.

Further, inhibiting the activity of a PLK protein is inhibiting the activity of a PLK3 protein.

The present invention further provides a method for detecting an HIV and/or SIV-infected cell, where the method includes enabling the cell to release a large number of detectable progeny viruses by inhibiting the activity of a PLK protein in the infected cell, so as to achieve the purpose of detection.

The present invention further provides a method for clearing an HIV and/or SIV-infected cell, where the method includes enabling the HIV and/or SIV-infected cell to release a large number of progeny viruses by inhibiting the activity of a PLK protein in the HIV and/or SIV-infected cell, and then specifically recognizing the viruses by a human immune system or recognizing the viruses by a related antiviral drug, so as to achieve the purpose of clearing the HIV and/or SIV-infected cell.

Further, according to the methods for detecting and clearing an HIV and/or SIV-infected cell, the HIV and/or SIV-infected cell includes: HIV and/or SIV-infected cells, as well as HIV and/or SIV-infected peripheral blood cells, CD4+T cells, natural killer cells, macrophages, dendritic cells and neurogliocytes.

Further, according to the methods for detecting and clearing an HIV and/or SIV-infected cell, inhibiting the activity of a PLK protein in the method is inhibiting the activity of a PLK3 protein.

The present invention further provides a method for directly inhibiting the release of viruses in an HIV and/or SIV-infected cell, where according to the method, the release of viruses in an HIV and/or SIV-infected cell can be directly inhibited by enhancing the activity of a PLK protein.

Preferably, according to the method for directly inhibiting the release of viruses in an HIV and/or SIV-infected cell, the HIV and/or SIV-infected cell includes: HIV and/or SIV-infected peripheral blood cells, CD4+T cells, natural killer cells, macrophages, dendritic cells and neurogliocytes.

Further, according to the method for directly inhibiting the release of viruses in an HIV and/or SIV-infected cell, enhancing the activity of a PLK protein in the method is enhancing the activity of a PLK3 protein.

Compared with the prior art, the present invention has the following beneficial effects.

A new target associated with the release of viruses in an HIV and/or SIV-infected cell is found for the first time in the present invention. By inhibiting the activity of a PLK3 protein or clearing the same, the purpose of releasing a large number of progeny viruses without activating a repository is achieved, such that the viruses can be detected in a physiological state and can also be recognized and cleared by the immune system or a related antiviral drug in vivo. According to previous detection methods, cells are strongly activated in vitro, resulting in changes of physiological (resting) characteristics of infected cells. In addition, as the size of a repository is overestimated because whether proviruses are complete cannot be distinguished, detection results are not realistic and accurate enough, and the methods cannot be used in clinical application.

Meanwhile, it is found by the present invention for the first time that enhancing the activity of the PLK3 protein can directly inhibit the release of viruses in an HIV and/or SIV-infected cell, and the purpose of permanently trapping the viruses in the cell can be achieved. Therefore, either inhibiting the activity of the PLK3 protein or clearing the same, or enhancing the activity of the PLK3 protein is beneficial for antiviral therapy of HIV infection.

In summary, the present invention provides a new theoretical basis and a new target for diagnosis and antiviral therapy of HIV and/or SIV infection. In addition, the present invention can effectively shorten a window period of virus detection, and a small number of infectious viruses can be detected at a cellular level at an extremely early stage of infection, so that medication basis and guarantee are provided for early diagnosis and extremely early treatment of HIV and/or SIV infection, and an important clinical application value is achieved.

BRIEF DESCRIPTION OF THE DRAWINGS

FIG. 15 is a diagram showing comparison of the content of SIV$_{agm}$ in a supernatant after transfection with PLK1, PLK2, PLK3, PLK4 and PLK5 protein expression vectors.

FIGS. 16A-16B are diagrams showing effect of a PLK3 kinase inhibitor, GW843682X, on HIV-1 infection.

DETAILED DESCRIPTION OF THE EMBODIMENTS

The present invention is described in detail below in combination with specific embodiments, for the purpose of making technical contents better understood by the public, rather than limiting the technical contents. Actually, improvements made according to same or similar principles are within the scope of protection of claims of the present invention.

Example 1

A human PLK3 protein in HIV repository cells has the effect of inhibiting translation of an HIV-1 virus protein and has a specific inhibition effect on HIV-1.

Figure 1:
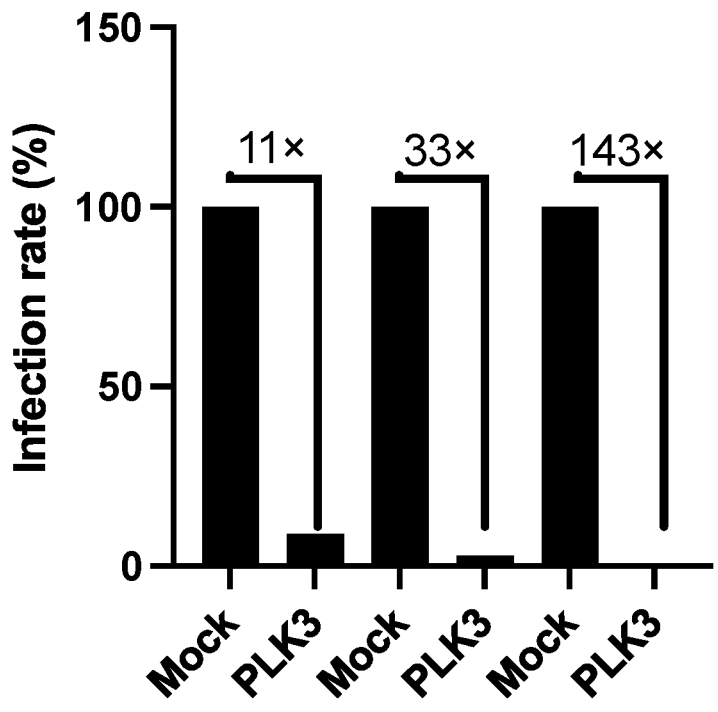
FIG. 1 is a diagram showing comparison of the infection rate of HIV in a supernatant after transfection with a PLK3 protein expression vector.

In order to verify the effects of PLK3, 293T cells with different PLK3 protein expression levels were treated with an HIV-1 virus vector, and it was found that compared with 293T cells without PLK3 protein expression, the HIV infectivity of the 293T cells with PLK3 protein expression was reduced to a maximum of about 1/50 of an original level. Specific test steps are as follows. 293T cells were transfected with a 3× FLAG-labeled PLK3 protein expression vector, and including a negative control group, were treated with pNL4.3. After the transfection was performed for 48 hours, a supernatant was used for infecting TZM-bl reporter cells to obtain virus infection levels. Data measured each time were obtained by subtracting background RLU (FIG. 1).

Figure 2:
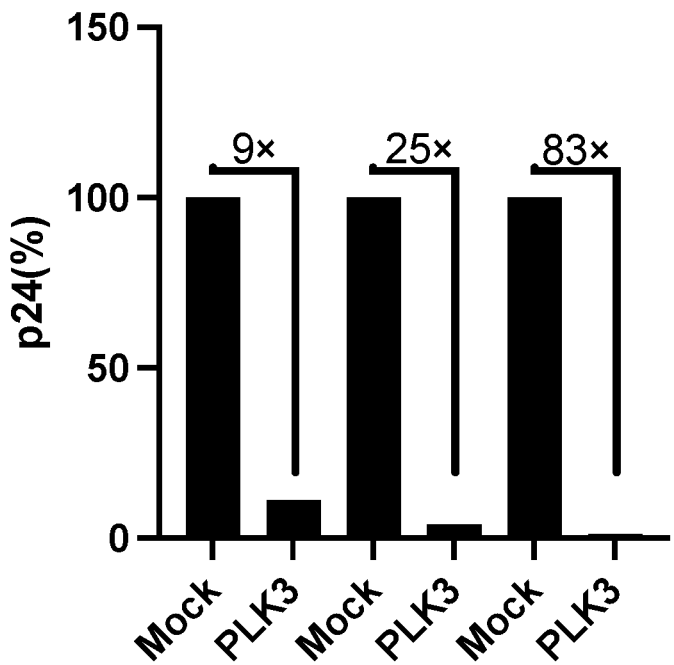
FIG. 2 is a diagram showing comparison of the content of p24 after transfection with a PLK3 protein expression vector.
Figure 3:
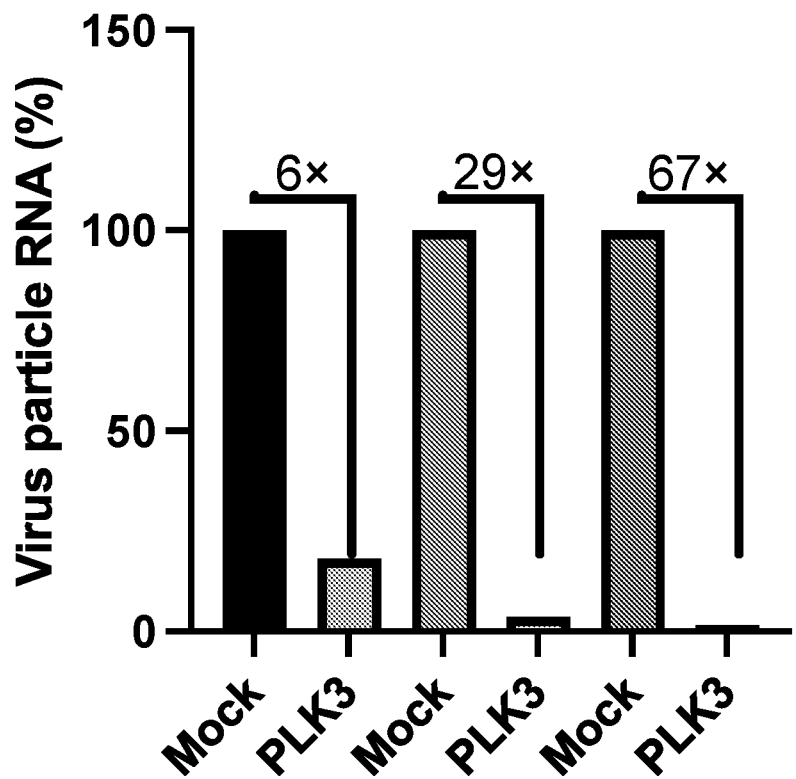
FIG. 3 is a diagram showing comparison of the content of genomic RNA associated with virus particles after transfection with a PLK3 protein expression vector.

In the case of overexpression of the PLK3 protein, the contents of a core antigen p24 of virus particles and genomic RNA of the virus particles in a cultured supernatant were also greatly decreased. Specific test steps are as follows. Similar to pretreatment steps shown in FIG. 1, p24 enzyme-linked immunosorbent assay (ELISA) was performed (FIG. 2), and qPCR based on a specific probe was performed to measure genomic RNA associated with virus particles (FIG. 3).

Figure 4:
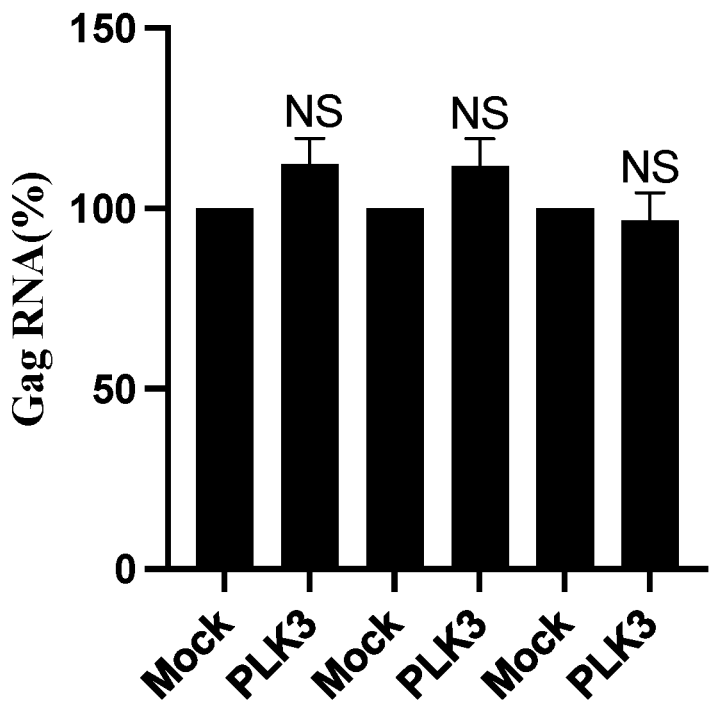
FIG. 4 is a diagram showing comparison of the content of HIV Gag RNA after transfection with a PLK3 protein expression vector.
Figure 5:
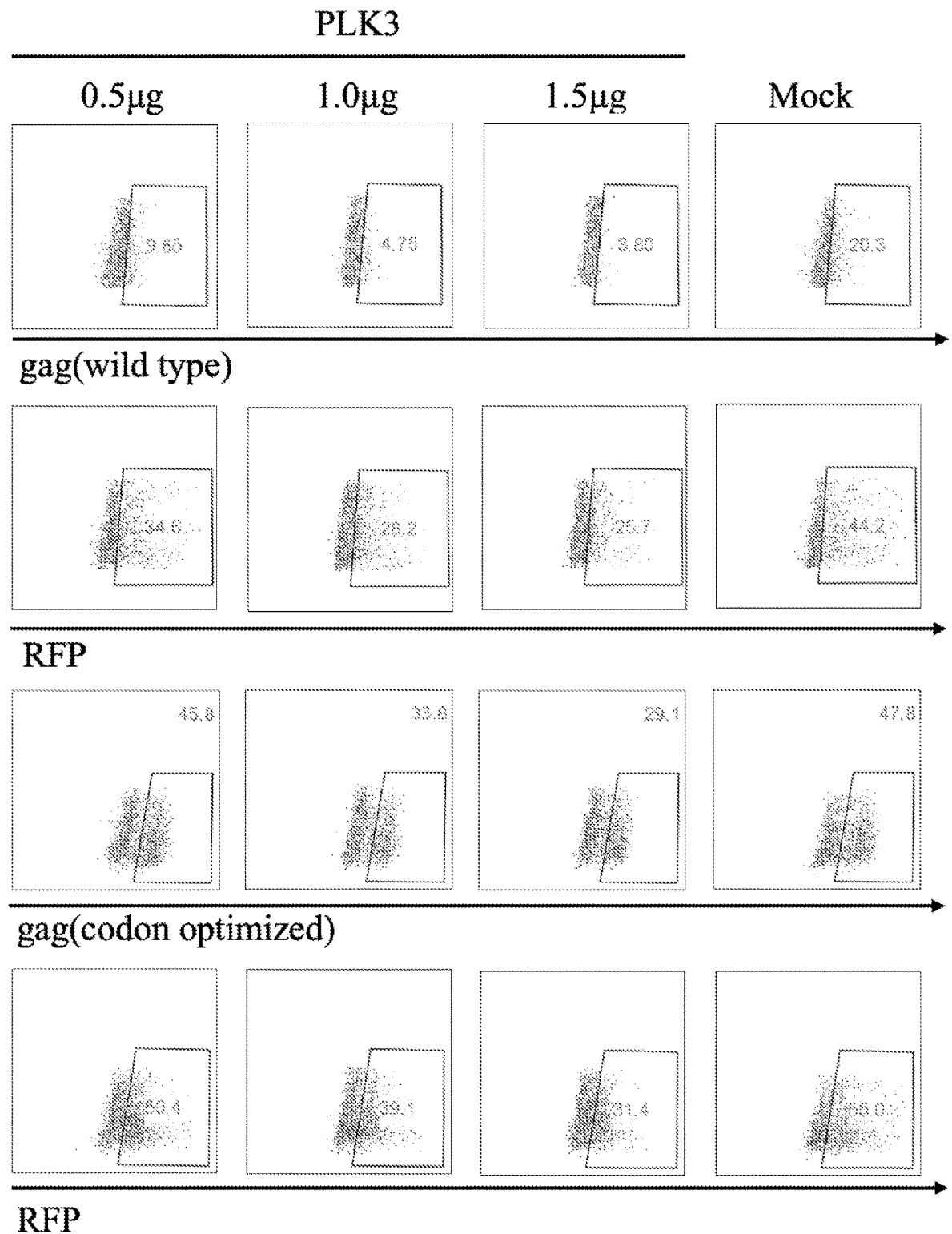
FIG. 5 is a diagram showing comparison of the contents of a wild type Gag protein and a codon optimized Gag protein after transfection with a PLK3 protein expression vector.

However, the transcription level of a virus Gag in cells was not affected by the overexpression of the PLK3 protein. It was indicated that the overexpression of the PLK3 protein obviously reduced the expression of the HIV-1 protein without affecting the transcription of HIV-1. Meanwhile, the virus Gag protein associated with the PLK3 protein was also obviously reduced, indicating that the PLK3 was involved in the process of specifically inhibiting the translation of the HIV protein. Specific test steps are as follows. All RNAs were extracted for qPCR to measure the Gag transcription level of HIV-1 (FIG. 4). Cells were collected for a flow cytometry test, and the expression level of an HIV-1 p24 protein was detected by using specific antibodies (FIG. 5).

Figure 6:
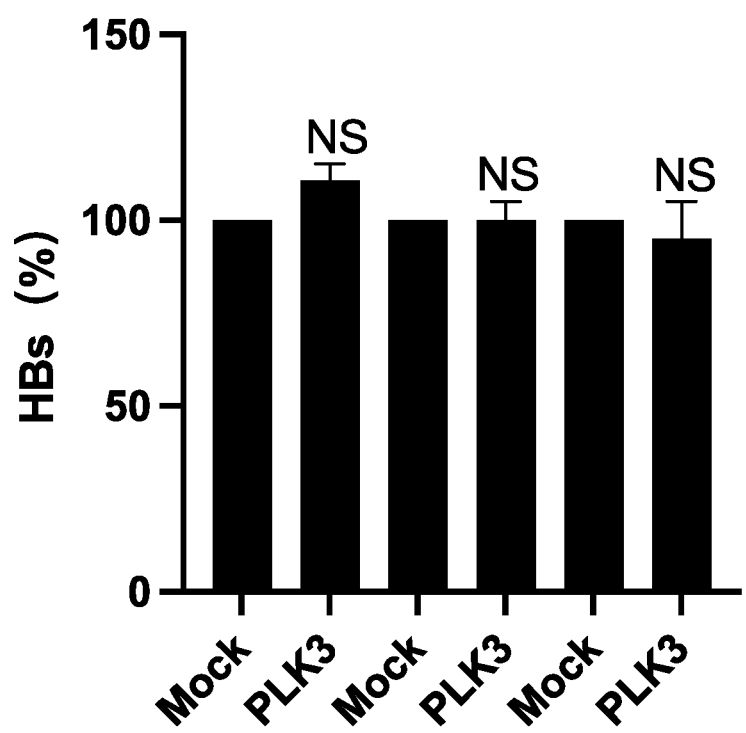
FIG. 6 is a diagram showing comparison of the content of HBV in a supernatant after transfection with a PLK3 protein expression vector.

Effects of the overexpression of the PLK3 protein in 293T cells on a hepatitis B virus (HBV) driven by a CMV promoter were detected to determine whether the PLK3 protein acted specifically on HIV-1. Results show that complete HBV replication is found, and that is to say, replication and release of the HBV are not affected by the PLK3 protein. Specific test steps are as follows. 293T cells in an experimental group were transfected with a 3× FLAG-labeled PLK3 expression vector, and including a negative control group, were treated with an HBV replicator (CMV promoter). After 48 hours, HBV virus particles in a cultured supernatant were measured by HBs enzyme-linked immunosorbent assay (FIG. 6).

Example 2

In a human PLK (PLK1, PLK2, PLK3, PLK4 and PLK5) protein family, only a PLK3 protein has the effect of inhibiting the translation of an HIV-1 protein and has a specific inhibition effect on HIV-1. Meanwhile, a chimpanzee PLK3 protein also has the effect of inhibiting the translation of an HIV-1 protein and has a specific inhibition effect on HIV-1.

Figure 7:
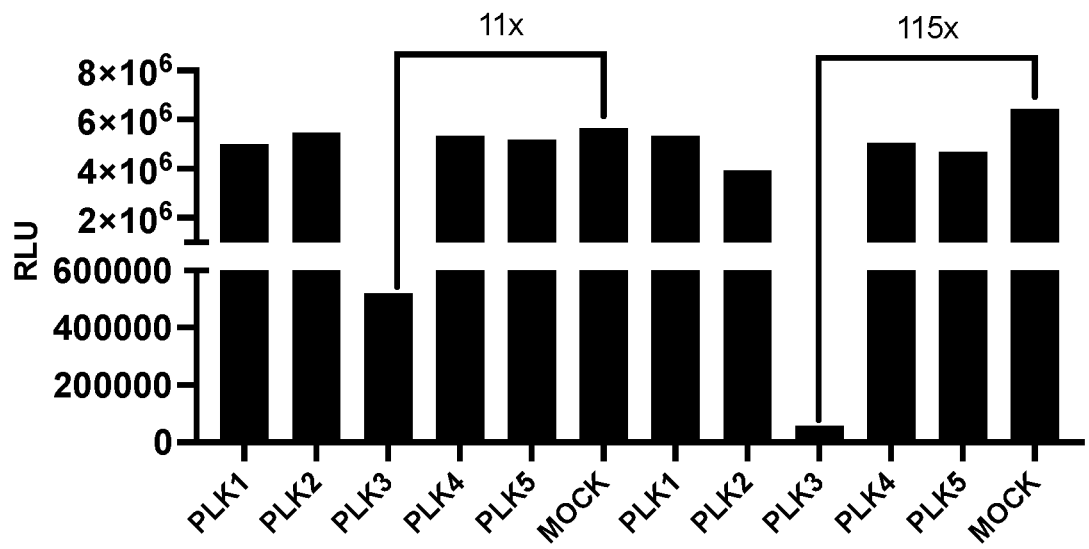
FIG. 7 is a diagram showing comparison of the content of HIV-1 in a supernatant after transfection of 293T cells with PLK1, PLK2, PLK3, PLK4 and PLK5 protein expression vectors.
Figure 8:
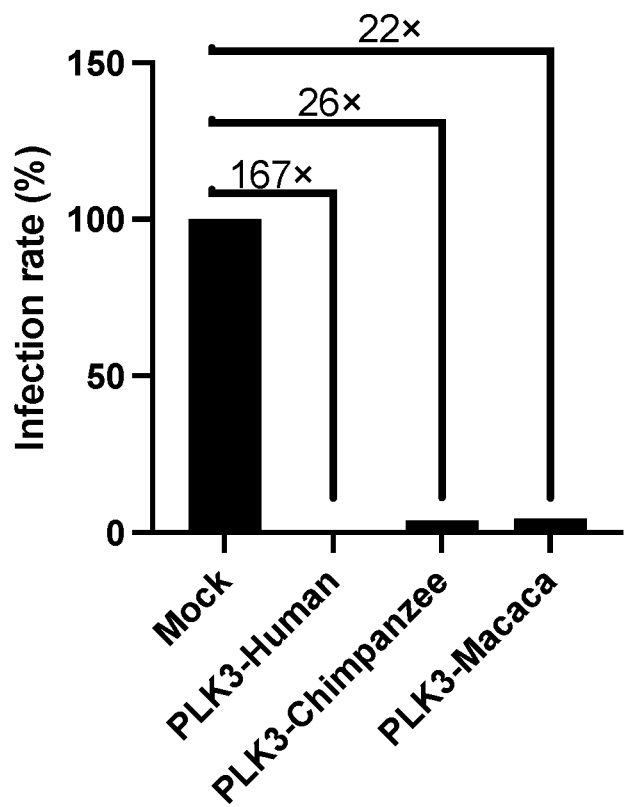
FIG. 8 is a diagram showing comparison of the content of HIV-1 in a supernatant after transfection with a PLK3 protein expression vector.

Human PLK proteins specifically include the following five types: a PLK1 protein, a PLK2 protein, a PLK3 protein, a PLK4 protein and a PLK5 protein. The anti-HIV-1 activity of all the five human PLK proteins and primate PLK3 proteins was detected. Compared with a negative control group, the HIV-1 infectivity was reduced by human PLK3 with different expression amounts to 1/11 and 1/115 of that of the negative control group. The human PLK1 protein, the PLK2 protein, the PLK4 protein and the PLK5 protein did not show anti-HIV-1 activity. A chimpanzee PLK3 protein and a macaca PLK3 protein can also reduce the HIV-1 infectivity, but have slightly different reduction degrees compared with the human PLK3 protein. It is indicated that all primate PLK3 family proteins may have anti-HIV-1 activity. Specific test steps are as follows: 293T cells were transfected with 3× FLAG-labeled human PLK1, PLK2, PLK3, PLK4 and PLK5 protein expression vectors, a 3× FLAG-labeled chimpanzee PLK3 protein expression vector and a 3× FLAG-labeled macaca PLK3 protein expression vector, respectively, and including a negative control group, were treated with pNL4.3. After the transfection was performed for 48 hours, a supernatant was used for infecting TZM-bl reporter cells to obtain virus infection levels. Data measured each time were obtained by subtracting background RLU (FIG. 7 and FIG. 8).

Example 3

A PLK3 protein has an inhibition effect on HIV-1, which is reflected in an inhibition effect on HIV wrapped by CXCR4 and CCR5 tropic envelope proteins without affecting the transcription of Gag.

Figure 9:
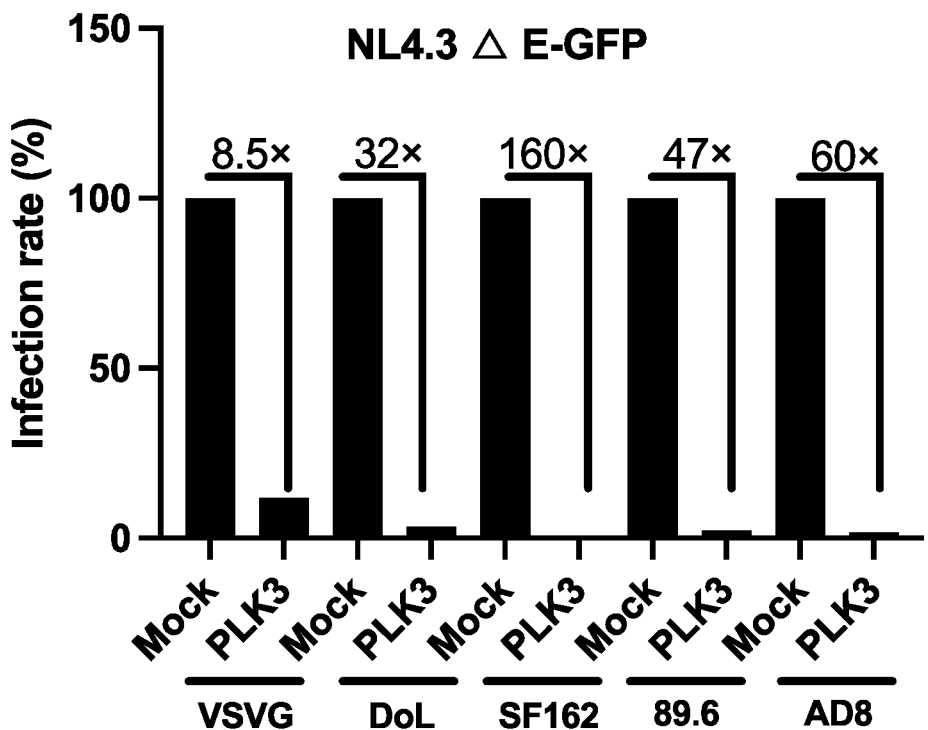
FIG. 9 is a diagram showing comparison of the contents of different envelope (VSV-G, HIV-1$_{DoL}$, HIV-1$_{SF162}$, HIV-1$_{89.6}$ and HIV-1$_{AD8}$) viruses in a supernatant after transfection with a PLK3 protein expression vector.
Figure 10:
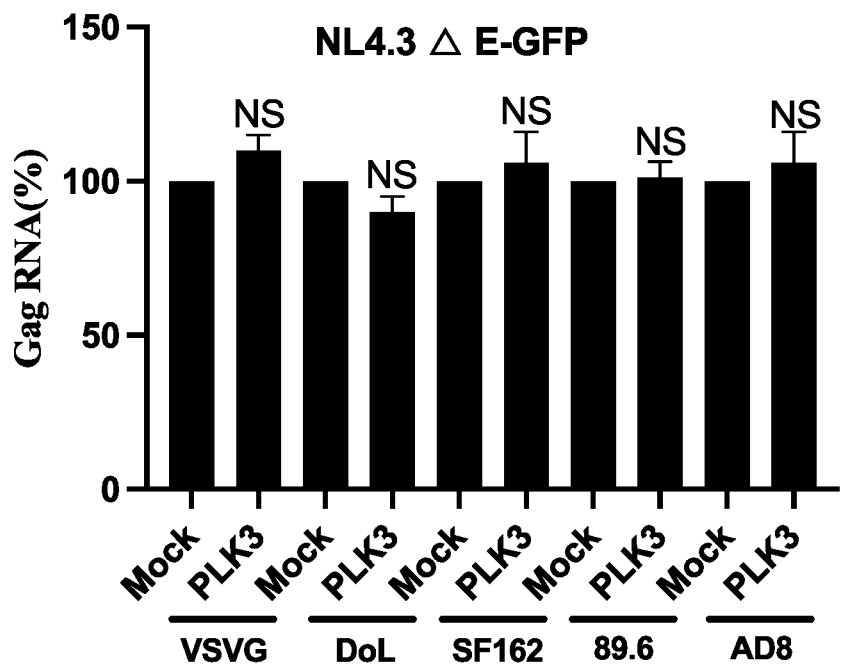
FIG. 10 is a diagram showing comparison of the content of HIV Gag RNA after transfection with a PLK3 protein expression vector.

A human PLK3 protein has an extremely strong ability to block HIV-1 infection without affecting the transcription of Gag Specific test steps are as follows. 293T cells were transfected with a 3× FLAG-labeled PLK3 protein expression vector, and including a negative control group, were treated with pNL4.3ΔE-GFP and vectors expressing VSV-G, pDoL-gp160, pSF162-gp160, pAD8-gp160 or p89.6-gp160, respectively. After the transfection was performed for 48 hours, a supernatant was used for infecting TZM-bl reporter cells to obtain virus infection levels. Data measured each time were obtained by subtracting background RLU (FIG. 9). All RNAs extracted were subjected to qPCR to quantify a Gag transcript, followed by normalization with phosphoglyceraldehyde dehydrogenase (FIG. 10).

Example 4

A PLK3 protein has an inhibition effect on HIV-1, HIV-2 and SIV, which is reflected in an inhibition effect on wild type CCR5 tropic viruses (AD8 and BaL), a bitropic virus (89.6), HIV-2$_{ROD}$ and SIV$_{agm}$.

Figure 11:
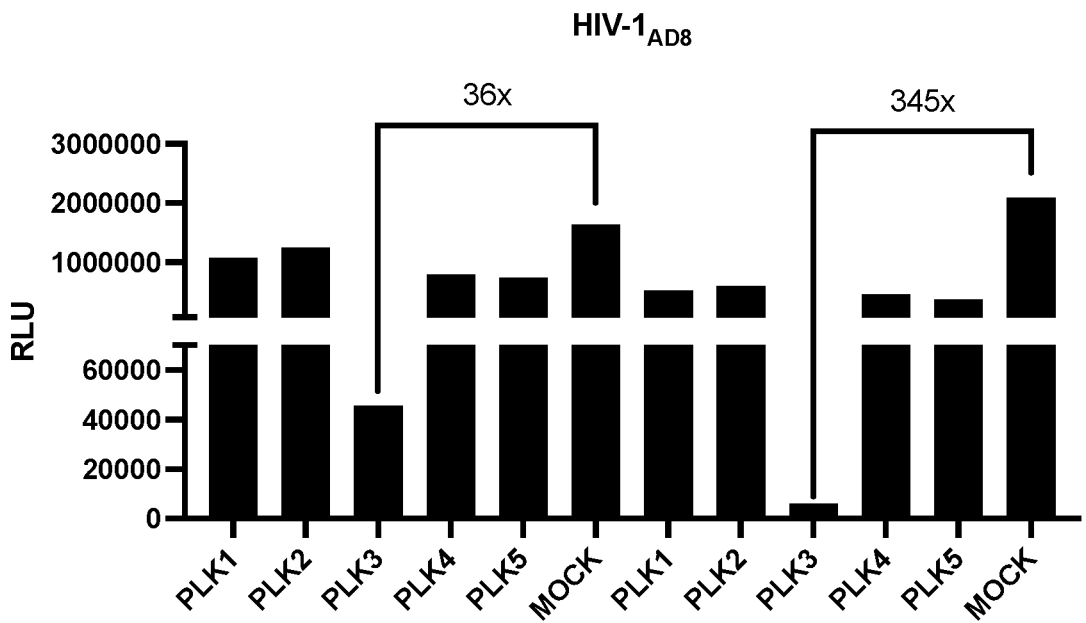
FIG. 11 is a diagram showing comparison of the content of CCR5 tropic HIV-1$_{AD8}$ in a supernatant after transfection with PLK1, PLK2, PLK3, PLK4 and PLK5 protein expression vectors.
Figure 12:
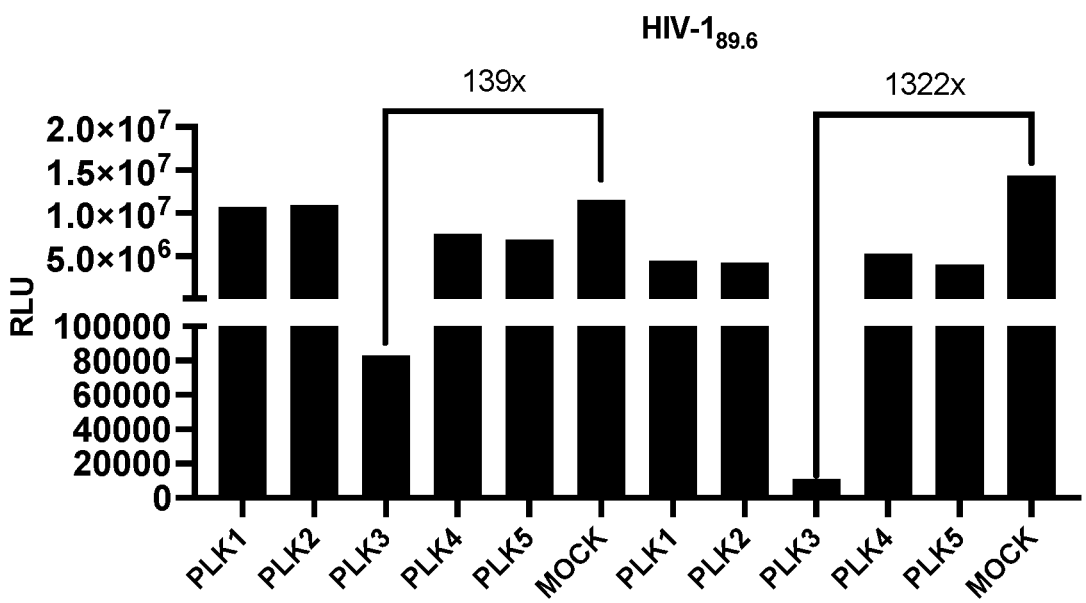
FIG. 12 is a diagram showing comparison of the content of CCR5 and CXCR4 (bitropic) HIV-1$_{89.6}$ in a supernatant after transfection with PLK1, PLK2, PLK3, PLK4 and PLK5 protein expression vectors.
Figure 13:
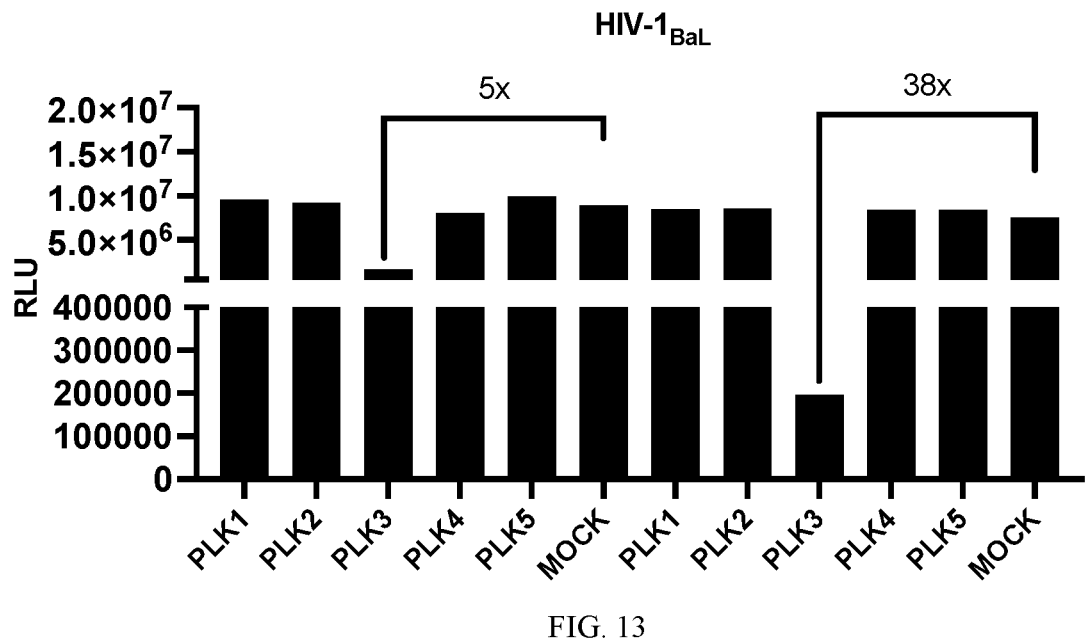
FIG. 13 is a diagram showing comparison of the content of CCR5 tropic HIV-1$_{BaL}$ in a supernatant after transfection with PLK1, PLK2, PLK3, PLK4 and PLK5 protein expression vectors.
Figure 14:
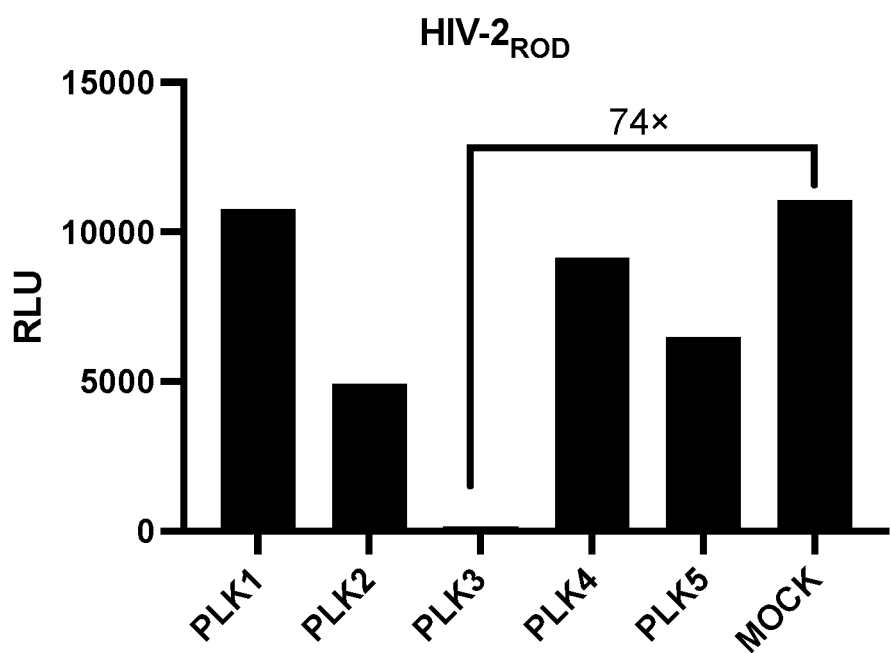
FIG. 14 is a diagram showing comparison of the content of HIV-2$_{ROD}$ in a supernatant after transfection with PLK1, PLK2, PLK3, PLK4 and PLK5 protein expression vectors.

The expression of human PLK3 also has an ability to limit infection with HIV-1$_{AD8}$, HIV-1$_{BaL}$, HIV-1$_{89.6}$, HIV-2$_{ROD}$ and SIV$_{agm}$. Specific test steps are as follows. 293T cells were transfected with a 3× FLAG-labeled PLK3 protein expression vector, and including a negative control group, were treated with virus vectors pAD8 (FIG. 11), p89.6 (FIG. 12), pBaL (FIG. 13), pHIV-2$_{ROD}$ (FIG. 14) and pSIV$_{agm}$ (FIG. 15), respectively. After the transfection was performed for 48 hours, a supernatant was used for infecting TZM-bl reporter cells to obtain virus infection levels. Data measured each time were obtained by subtracting background RLU.

Example 5

PLK3 requires the kinase activity to achieve an inhibition effect on HIV-1. PLK3 kinase inhibitors or kinase domain defective mutants can inhibit the inhibition effect of PLK3 on HIV-1.

Figure 17:
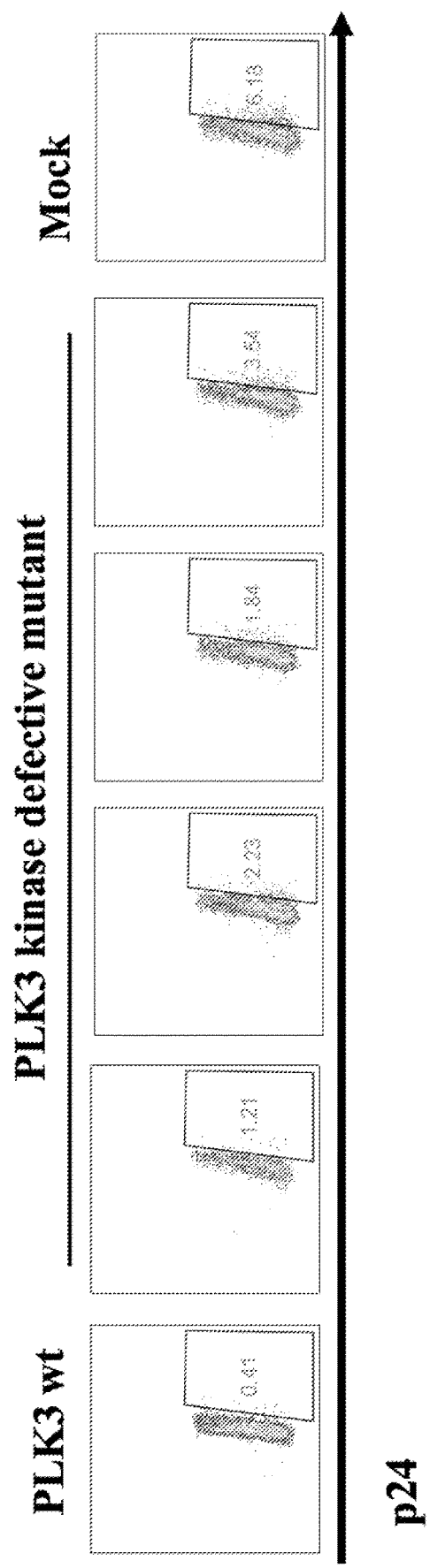
FIG. 17 is a diagram showing effect of a PLK3 kinase defective mutant expression vector on HIV-1 infection after transfection.

Human PLK3 is Polo-like kinase. Through treatment with a PLK3 kinase inhibitor, GW843682X, although the expression level of PLK3 is not changed, the antiviral ability is inhibited. Treatment was performed with GW843682X or a PLK3 kinase domain mutant vector, respectively, and results were observed. The GW843682X or the PLK3 kinase domain mutant can inhibit the anti-HIV-1 ability of human PLK3. Specific test steps are as follows. Cells were transfected with a 3× FLAG-labeled PLK3 protein expression vector, and including a negative control group, were treated with NL4.3.Luc (VSV-G) after 24 hours. Meanwhile, the cells were also treated with GW843682X. After the transfection was performed for 48 hours, the cells were collected for a flow cytometry test (FIGS. 16A-16B). Cells were transfected with a 3× FLAG-labeled PLK3 kinase domain defective mutant protein expression vector, and including a negative control group, were treated with NL4.3.Luc (VSV-G) after 24 hours. After the transfection was performed for 48 hours, the cells were collected for a flow cytometry test (FIG. 17).

What is claimed is:

1. An in vitro method of enhancing an expression of a PLK3 protein in an HIV-infected cell comprising the step of transfecting the HIV-infected cell with a PLK3 protein expression vector; wherein the PLK3 protein is a PLK3-201 protein, and the PLK3-201 protein has the amino acid sequence shown in SEQ ID NO: 1.

2. The in vitro method according to claim 1, wherein the HIV-infected cell comprises: peripheral blood cells, CD4+T cells, natural killer cells, macrophages, dendritic cells, and neurogliocytes.

* * * * *

SEQUENCE LISTING

```
<160> NUMBER OF SEQ ID NOS: 1

<210> SEQ ID NO 1
<211> LENGTH: 646
<212> TYPE: PRT
<213> ORGANISM: Homo sapiens

<400> SEQUENCE: 1

Met Glu Pro Ala Ala Gly Phe Leu Ser Pro Arg Pro Phe Gln Arg Ala
1               5                   10                  15

Ala Ala Ala Pro Ala Pro Pro Ala Gly Pro Gly Pro Pro Pro Ser Ala
            20                  25                  30

Leu Arg Gly Pro Glu Leu Glu Met Leu Ala Gly Leu Pro Thr Ser Asp
        35                  40                  45

Pro Gly Arg Leu Ile Thr Asp Pro Arg Ser Gly Arg Thr Tyr Leu Lys
    50                  55                  60

Gly Arg Leu Leu Gly Lys Gly Gly Phe Ala Arg Cys Tyr Glu Ala Thr
65                  70                  75                  80

Asp Thr Glu Thr Gly Ser Ala Tyr Ala Val Lys Val Ile Pro Gln Ser
                85                  90                  95

Arg Val Ala Lys Pro His Gln Arg Glu Lys Ile Leu Asn Glu Ile Glu
            100                 105                 110

Leu His Arg Asp Leu Gln His Arg His Ile Val Arg Phe Ser His His
        115                 120                 125

Phe Glu Asp Ala Asp Asn Ile Tyr Ile Phe Leu Glu Leu Cys Ser Arg
    130                 135                 140

Lys Ser Leu Ala His Ile Trp Lys Ala Arg His Thr Leu Leu Glu Pro
145                 150                 155                 160

Glu Val Arg Tyr Tyr Leu Arg Gln Ile Leu Ser Gly Leu Lys Tyr Leu
                165                 170                 175

His Gln Arg Gly Ile Leu His Arg Asp Leu Lys Leu Gly Asn Phe Phe
            180                 185                 190

Ile Thr Glu Asn Met Glu Leu Lys Val Gly Asp Phe Gly Leu Ala Ala
```

-continued

```
            195                 200                 205
Arg Leu Glu Pro Pro Glu Gln Arg Lys Lys Thr Ile Cys Gly Thr Pro
210                 215                 220

Asn Tyr Val Ala Pro Glu Val Leu Leu Arg Gln Gly His Gly Pro Glu
225                 230                 235                 240

Ala Asp Val Trp Ser Leu Gly Cys Val Met Tyr Thr Leu Leu Cys Gly
                    245                 250                 255

Ser Pro Pro Phe Glu Thr Ala Asp Leu Lys Glu Thr Tyr Arg Cys Ile
                260                 265                 270

Lys Gln Val His Tyr Thr Leu Pro Ala Ser Leu Ser Leu Pro Ala Arg
            275                 280                 285

Gln Leu Leu Ala Ala Ile Leu Arg Ala Ser Pro Arg Asp Arg Pro Ser
290                 295                 300

Ile Asp Gln Ile Leu Arg His Asp Phe Phe Thr Lys Gly Tyr Thr Pro
305                 310                 315                 320

Asp Arg Leu Pro Ile Ser Ser Cys Val Thr Val Pro Asp Leu Thr Pro
                325                 330                 335

Pro Asn Pro Ala Arg Ser Leu Phe Ala Lys Val Thr Lys Ser Leu Phe
                340                 345                 350

Gly Arg Lys Lys Lys Ser Lys Asn His Ala Gln Glu Arg Asp Glu Val
            355                 360                 365

Ser Gly Leu Val Ser Gly Leu Met Arg Thr Ser Val Gly His Gln Asp
370                 375                 380

Ala Arg Pro Glu Ala Pro Ala Ala Ser Gly Pro Ala Pro Val Ser Leu
385                 390                 395                 400

Val Glu Thr Ala Pro Glu Asp Ser Ser Pro Arg Gly Thr Leu Ala Ser
                405                 410                 415

Ser Gly Asp Gly Phe Glu Glu Gly Leu Thr Val Ala Thr Val Val Glu
                420                 425                 430

Ser Ala Leu Cys Ala Leu Arg Asn Cys Ile Ala Phe Met Pro Pro Ala
            435                 440                 445

Glu Gln Asn Pro Ala Pro Leu Ala Gln Pro Glu Pro Leu Val Trp Val
450                 455                 460

Ser Lys Trp Val Asp Tyr Ser Asn Lys Phe Gly Phe Gly Tyr Gln Leu
465                 470                 475                 480

Ser Ser Arg Arg Val Ala Val Leu Phe Asn Asp Gly Thr His Met Ala
                485                 490                 495

Leu Ser Ala Asn Arg Lys Thr Val His Tyr Asn Pro Thr Ser Thr Lys
                500                 505                 510

His Phe Ser Phe Ser Val Gly Ala Val Pro Arg Ala Leu Gln Pro Gln
            515                 520                 525

Leu Gly Ile Leu Arg Tyr Phe Ala Ser Tyr Met Glu Gln His Leu Met
530                 535                 540

Lys Gly Gly Asp Leu Pro Ser Val Glu Glu Val Glu Val Pro Ala Pro
545                 550                 555                 560

Pro Leu Leu Leu Gln Trp Val Lys Thr Asp Gln Ala Leu Leu Met Leu
                565                 570                 575

Phe Ser Asp Gly Thr Val Gln Val Asn Phe Tyr Gly Asp His Thr Lys
                580                 585                 590

Leu Ile Leu Ser Gly Trp Glu Pro Leu Leu Val Thr Phe Val Ala Arg
            595                 600                 605

Asn Arg Ser Ala Cys Thr Tyr Leu Ala Ser His Leu Arg Gln Leu Gly
610                 615                 620
```

-continued

```
Cys Ser Pro Asp Leu Arg Gln Arg Leu Arg Tyr Ala Leu Arg Leu Leu
625                 630                 635                 640

Arg Asp Arg Ser Pro Ala
                645
```